(12) United States Patent
Volker

(10) Patent No.: US 9,995,658 B2
(45) Date of Patent: Jun. 12, 2018

(54) SAMPLING POINT VALVE

(71) Applicant: Fidica GmbH & Co. KG, Sailauf (DE)

(72) Inventor: Manfred Volker, Blankenbach (DE)

(73) Assignee: Fidica GmbH & Co. KG, Sailauf (DE)

( * ) Notice: Subject to any disclaimer, the term of this patent is extended or adjusted under 35 U.S.C. 154(b) by 21 days.

(21) Appl. No.: 15/059,551

(22) Filed: Mar. 3, 2016

(65) Prior Publication Data
US 2016/0258847 A1 Sep. 8, 2016

(30) Foreign Application Priority Data

Mar. 5, 2015 (DE) .................. 10 2015 002 854

(51) Int. Cl.
| G01N 1/00 | (2006.01) |
| G01N 1/20 | (2006.01) |
| C12M 1/12 | (2006.01) |
| F16K 37/00 | (2006.01) |
| G01K 5/48 | (2006.01) |
| C12M 1/00 | (2006.01) |

(52) U.S. Cl.
CPC .......... G01N 1/2035 (2013.01); C12M 29/00 (2013.01); C12M 37/00 (2013.01); F16K 37/0008 (2013.01); G01K 5/483 (2013.01); G01N 2001/205 (2013.01); G01N 2001/2071 (2013.01)

(58) Field of Classification Search
CPC .......... G01N 1/2035; G01N 2001/205; G01N 2001/2071; C12M 29/00; C12M 37/00; F16K 37/0008; G01K 5/483

USPC ..................... 73/863.86, 863.81, 864.01, 863
See application file for complete search history.

(56) References Cited

U.S. PATENT DOCUMENTS

| 4,448,147 A | * | 5/1984 | Dewaegheneire | ..... G01K 5/483 116/216 |
| 8,549,936 B2 | * | 10/2013 | Volker | ................... F16K 3/262 73/864.15 |
| 2012/0227845 A1 | * | 9/2012 | Salomon | ................ C12M 33/00 137/625 |

FOREIGN PATENT DOCUMENTS

| DE | 9317674 U1 | 4/1994 |
| DE | 20316936 U1 | 4/2004 |
| DE | 102006031840 A1 | 1/2008 |
| WO | 2006042825 A1 | 4/2006 |

* cited by examiner

Primary Examiner — Manish S Shah
Assistant Examiner — Nigel Plumb
(74) Attorney, Agent, or Firm — Greer, Burns & Crain, Ltd.

(57) ABSTRACT

The sampling point valve, with a valve body that is movable in a valve housing between a closed position and an open position of the sampling point valve, wherein the valve body has a sample fluid channel, characterized in that the valve body is made of a material with a high thermal conductivity coefficient, preferably metal, that a signal unit with an essentially pot-shaped housing part made of a material with a high thermal conductivity coefficient, preferably metal, is in contact with the valve body, and that the signal unit includes a signal button that can be advanced out of a housing by a shape memory spring device when this device is warmed.

10 Claims, 2 Drawing Sheets

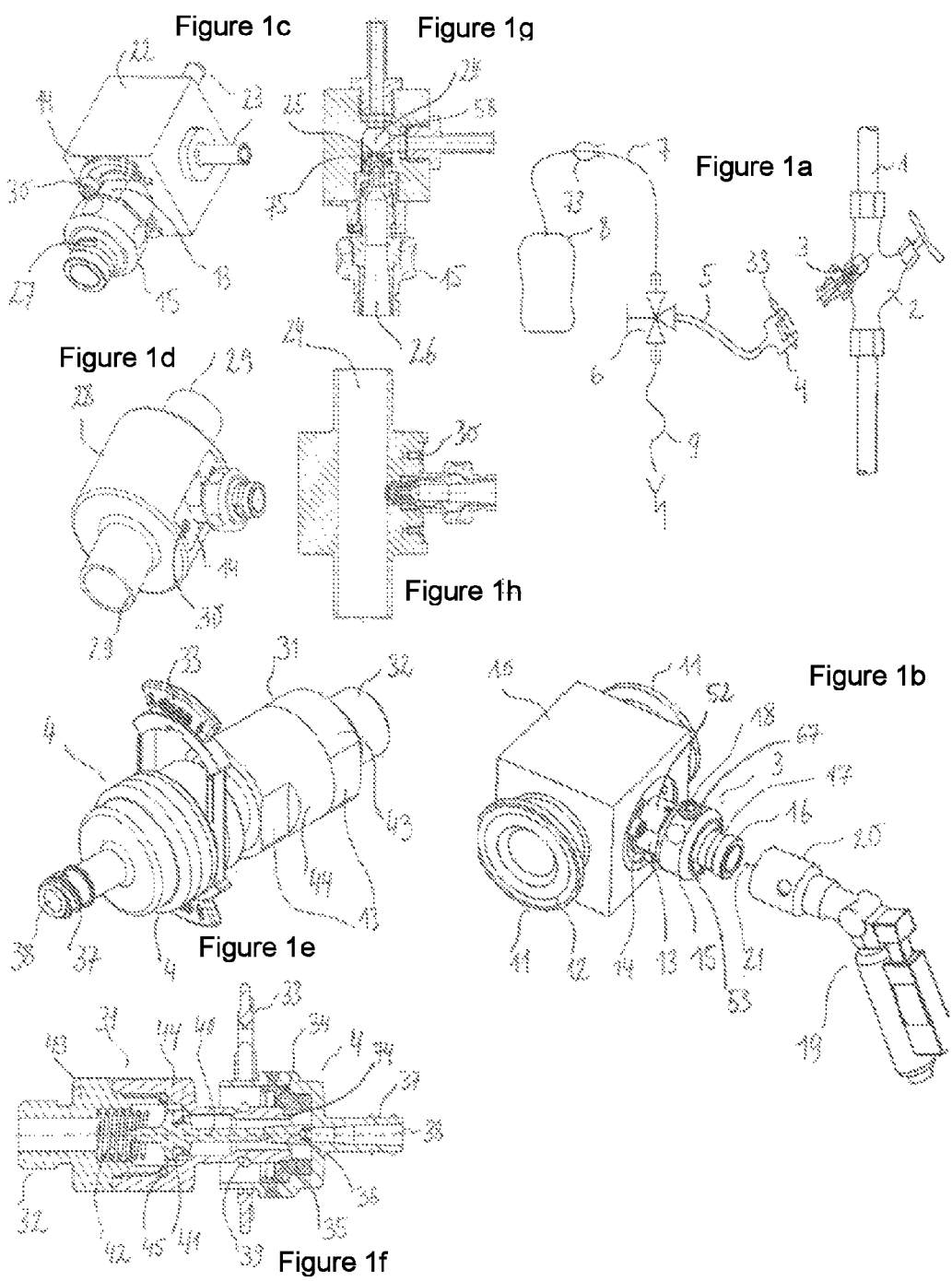

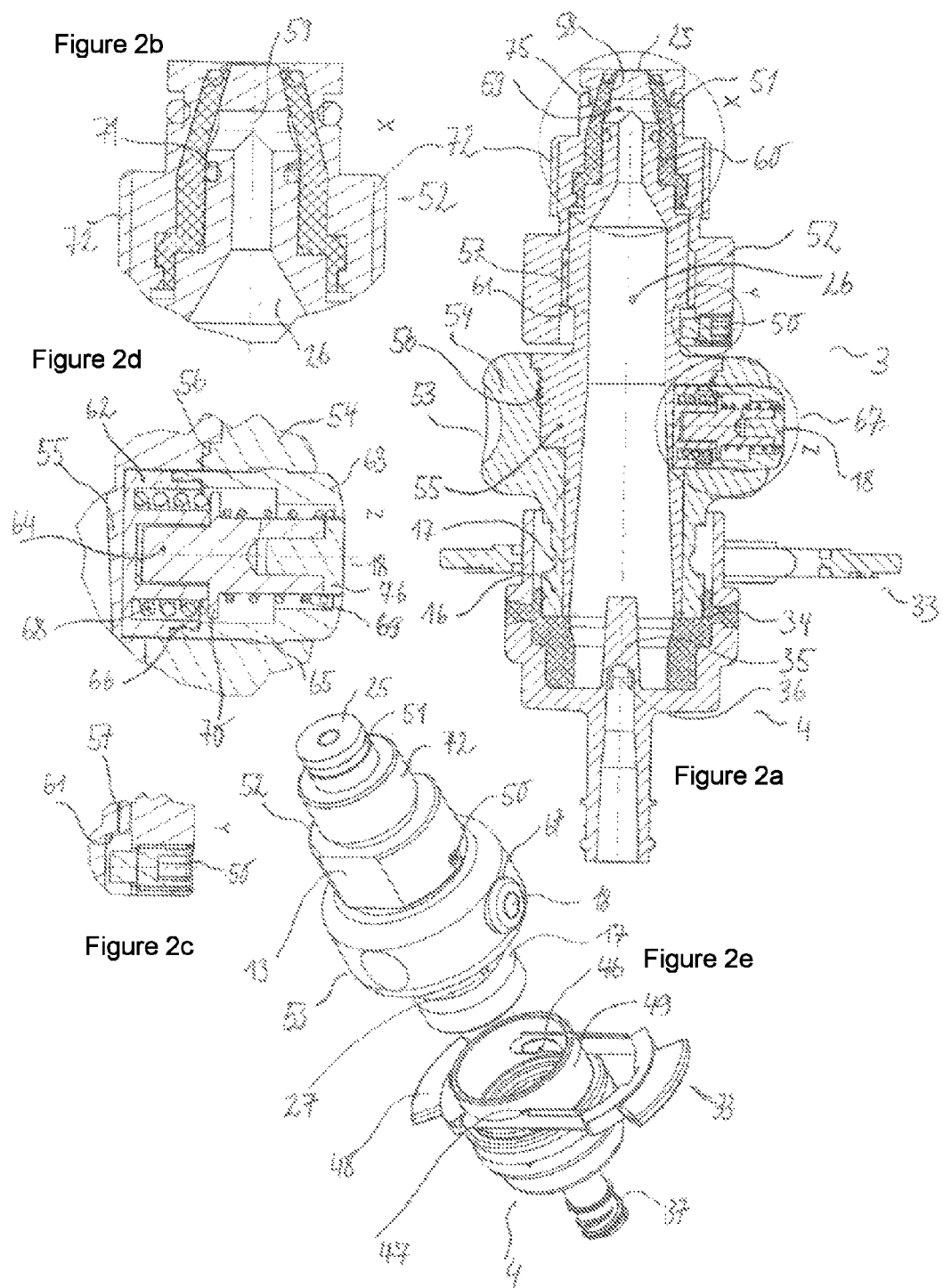

SAMPLING POINT VALVE

FIELD OF THE INVENTION

The object of this development is to develop a sampling device for fluids that, as far as possible, allows sampling without microbiological and/or chemical influence by the sampler or the design of the extraction unit.

BACKGROUND OF THE INVENTION

Sample fluids are extracted by means of a multitude of sampling point valves for the purpose of chemical and/or microbiological and also physical or other sensory identifications.

In many cases, the regulative and normative requirements regarding the microbiological and chemical limits are so strict that even small contaminations of the sample, e.g., at the site during the sampling, hinder or even make impossible demonstrable verification.

On the one hand this is due to the lack of freedom of dead space or also due to the poor cleaning possibility in the available designs.

Inadequate hygiene on the part of the sampler due to contact with fluid-carrying, high-purity components or also with the fluid sample itself lead to sample falsifications.

Further disadvantages that should not be overlooked are non-sterile sample containers, their identification, and their reliable transport to the laboratory.

SUMMARY OF THE INVENTION

The basis of the invention under consideration is to specify a sampling point valve that allows reliable, user-friendly sampling.

This object is solved according to the invention by a sampling point valve that comprises a valve body that can be moved in a valve housing between a closed position and an open position of the sampling point valve. The valve body has a sample fluid channel and the valve body is made of a material with a high thermal conductivity coefficient, preferably a metal. The signal valve further comprises a signal unit with an essentially pot-shaped housing part made of a material with a high thermal conductivity coefficient, preferably metal, that is in contact with the valve body. The signal unit includes a signal button that can be advanced out of a housing by a shape memory spring device as it is heated.

Advantageous further developments of the invention are characterized herein below.

The invention provides for the valve body to be made of a material with a high thermal conductivity coefficient, preferably metal, and for a signal unit with a housing part to be in contact with the valve body, whereby this housing part is likewise made of a material with a high thermal conductivity coefficient. A suitable material is aluminum or an aluminum alloy.

The invention furthermore provides for the signal unit to include a signal button that can be advanced out of a housing by a spring device. The housing consists of the above-mentioned housing part made of the material with a high thermal conductivity coefficient and a connecting, essentially cylindrical housing part that is preferably made of plastic and that therefore is not or only barely heated.

The spring device can very advantageously be a shape memory spring that returns to its original shape when it cools.

It is very advantageously proposed that sitting on the outside of the valve body is a handle made of a heat-insulating material that prevents an operator from burning a hand during a sampling point valve flaming process.

In more detail, it is provided for a guide body, which is provided with a collar, to be arranged in the housing in a manner that allows it to be slid, and for the signal button to be attached to the free end of this guide body. The spring device, preferably a shape memory spring device, is supported on the base of the pot-shaped housing and on the collar.

It is furthermore possible for a reset spring to be arranged in the housing, whereby this reset spring has a smaller spring force than that of the shape memory spring and preloads the guide body into the retracted starting position.

The signal button can be a color that differs from that of the guide body. If, under corresponding heating of the valve body, the signal button and an end section of the guide body are advanced beyond the handle, this is clearly visible due to the different color of the guide body.

Great significance is attached here to the dead-space-free design and its evaluation with regard to the hygienic condition.

A special challenge is the manufacture of sterility that is as complete as possible in the fluid-carrying sampling channels before the extraction begins. In this process, utilization of flaming devices should not lead to any damages in the environment or to burns, and also not to an excessive use of primary energy.

An extraction technique is advantageously used that allows a reliable fluid flow into the sample container directly without air contact for problematic fluids as well.

The solution of the object is prepared by installing a valve or connection block with a receptacle for a sampling point valve into the fluid-carrying line.

The effective solution is that the fluid available for the sample flushes the sampling point valve on the extraction side without dead space.

In the closed state, a conical gasket face prevents the sample fluid from escaping.

In the open state, the sample fluid first flows through the sterilizable sample fluid channel, then to the sample container via a stick-on sterile connection adapter and a sterile disposable article that is to be connected thereto.

The sample fluid channel is advantageously to be sterilized with a center-adjustable flaming device through to the extraction point. With great advantage, the sterilization result can be visually evaluated on the basis of a signal button.

The movement of the signal button out of the resting position into the sterile position during the heating is caused by a spring that is made of a shape memory alloy, for example, NiTi (nickel titanium, nitinol).

Shape memory alloys are special metals that can exist in two different crystal structures. They are also often called memory metals. This is based on the phenomenon in which they can apparently "remember" an earlier shaping in spite of a subsequent strong deformation.

At the same time, there are alloys with a one-way effect, e.g., a one-time change of shape when heated. Shape memory alloys can also be used with a two-way effect. However this component is not able to do its work while cooling.

In the design according to the invention, both alloy forms can be used because a reset spring presses the signal button back into the resting position during the cooling process.

Other temperature-sensitive components, such as bimetals, for example, are also conceivable as alternatives to shape memory alloys.

Further advantages of the unit are the insulation protection and the resulting low surface temperature of the sampling point valve after the flaming process, the possible manual operation without tool associated with this low surface temperature, the conical gasket to the fluid-carrying line, the trumpet-shaped design of the sample fluid channel, which minimizes residual amounts, and the universal connection adapter for the sterile disposable article.

According to another aspect, a connection adapter is proposed which can be connected to different valves, whereby the adapter can be placed on the end sections of these.

The adapter has a bowl-shaped or pot-shaped housing on the bottom of which is placed a hose connection piece, whereby lying on the inside wall of the housing is a ring-shaped gasket whose inside diameter is larger in areas as the distance from the base of the housing increases.

At the same time, the ring-shaped gasket can have a plurality of cylindrical sections with different diameters, whereby at least one conically widening section can also be developed.

The adapter can thereby be placed on valves whose end sections have different diameters, so that in each case a sealed connection can be made between the adapter and the particular valve.

Particularly advantageously, it is proposed that the hose connection piece of the adapter continues to an axial bolt with closed front wall that runs into the interior of the bowl-shaped housing. In this way, the adapter is also suitable for connection to those valves that have a spring-pressurized closing element that must be pressed back in order to open the valve. When placing the adapter, this takes place by means of the inner axial bolt, which presses with its closed front wall against the closing element and transfers said closing element into the open position.

Advantageously developed in the circumferential wall of the bolt of the adapter is at least one opening for the entry of fluid, whereby the opening is connected to the interior of the hose connection piece, so that the fluid can flow off through a hose placed on the piece.

In order to lock the adapter placed on the valve in its attachment position, it is furthermore proposed that the bowl-shaped housing has, close to its free end, at diametrically opposed positions, two slots that run through the circumferential wall and in which two parallel bars of a locking device are run in such a manner that they can slide. On opposite positions of the bars, circular segments are advantageously cut away whose diameter agrees with the inside diameter of the bowl-shaped housing.

It is furthermore proposed that the ends of the parallel bars of the locking device are connected to curvilinear cross-bars whose inside diameter agrees with the outside diameter of the bowl-shaped housing. In this way, the cross-bars can form limit stops with which the bars are either positioned with the cut-away circular segments at the slots so that the adapter can be placed on the end section of a valve, or the bars protrude into the interior of the bowl-shaped housing so that the adapter is locked on the valve.

The curvilinear cross-sections can be provided with indication vanes for the particular locking state.

The clarification of the function and the explanation of the design follow as figure descriptions.

BRIEF DESCRIPTION OF THE DRAWINGS

FIG. 1a is a schematic view of a sampling system.

FIG. 1b is a perspective view of a connection block and flaming device.

FIG. 1c is a perspective view of the connection block.

FIG. 1d is a perspective view of another connection block.

FIG. 1e is a perspective view of a universal adapter and extraction coupler.

FIG. 1f is a longitudinal cross-section of the FIG. 1e universal adapter and extraction coupler.

FIG. 1g is a longitudinal cross-section of the FIG. 1c connection block.

FIG. 1h is a longitudinal cross-section of the FIG. 1d connection block.

FIG. 2a is a longitudinal cross-section of the sampling point valve and universal adapter.

FIG. 2b is an enlarged detail of the circle X in FIG. 2a.

FIG. 2c is an enlarged detail of the circle Y in FIG. 2a.

FIG. 2d is an enlarged detail of the circle Z in FIG. 2a.

FIG. 2e is a perspective view of the sampling point valve and universal adapter uncoupled.

DETAILED DESCRIPTION OF PREFERRED EMBODIMENTS

FIG. 1a here shows the principle of a complete sampling step.

Installed into the fluid-carrying line (1) above the gate valve is a cut-off valve (2) with a mounting hole. The sampling point valve (3) can be attached in this mounting hole.

To extract the sample, the lockable universal adapter (4) is placed onto the sampling point valve (3) and fixed in place in a sealing manner by moving the locking device (33).

When the sampling point valve (3) is open, the sample fluid flows to the three-way valve (6) via a connection line (5); initially a part of the sample can be discarded via a flushing connection (9) before the sample container (8) is filled via a container connection (7) after reactivation of the three-way valve (6). Once the sample container (8) has been filled with the required quantity of sample fluid, a clamp (73) can be closed. The sampling point valve (3) is likewise closed and the universal adapter (4) is disconnected. The closed sample container (8) can be taken to the laboratory in a cooled container by means of glued-on identification data.

FIG. 1b shows a connection block (10) with dead-space-free clamp connections (11) that is to be detachably installed in a conduit or in another possible system. The two-piece sampling point valve (3) is screwed into a block (10) with its stationary attachment unit (52). In order for the gasket seat (75) to remain secured with respect to the fluid channel (24) during opening and closing procedures due to the rotational movement of the closing element (53), an anti-twisting lock (14) fixes the stationary attachment unit (52) in place.

The anti-twisting lock (14) is executed in a horseshoe shape and lies on the spanner flats (13) of the stationary attachment unit (52) on both sides.

The rotatable closing element (53) has a twist grip (15), whereby the signal unit (67) with a signal button (18) is mounted in the circumferential side of this twist grip.

A flaming device (19) with the centering sleeve (20) can be plugged onto the retaining sleeve (16) for the sample adapter, whereby (21) shows the contour of the flame that is centered directly in the sample liquid channel (26).

FIG. 1c shows an embodiment of a connection block (22) with hose connections (23). Discernible is the front face (25) of the sampling point valve (3), which protrudes directly into the fluid channel (24). A sealing cone (58) prevents fluid from escaping into the sample fluid channel (26).

FIG. 1d shows a connection block (28) with welded fittings (29) that can be executed in various diameters and consequently can be welded into pharmaceutical lines.

FIG. 1e depicts a possible adaption of the universal adapter (4) to an extraction coupler (31). As a rule, the extraction coupler (31) is screwed with a screw-in thread (32) into on-site fluid pipework.

The extraction coupler (31) consists of a fitting piece (44) which is screwed or welded to a closing piece (43) in a manner that forms a seal. Arranged in the interior are a star-shaped closing valve (40) with gasket (41) and pressure spring (42).

To extract sample fluid from the coupler (31), the universal adapter (4) with the staggered gasket (34) is pressed onto the fitting front piece (74). In this process an opening bolt (35) of the universal adapter (4) pushes the closing valve (40) backwards, so that sample fluid can flow into the channel for sample fluid (38) via the fluid channels (36). A connection line (5) can be attached to a hose connection (37). Due to the staggering of the gasket (34), the adapter (4) can be adapted to various diameters.

FIG. 2 shows, in an enlarged, more detailed depiction, the configuration of the sampling point valve (3), whose main components are a stationary attachment unit (52) and the rotatable closing element (53).

The stationary attachment unit (52) is to be screwed in with a screw thread (72), for example, into one of the previously mentioned applications. Latching or plug connections are also possible instead of a screw thread.

The end (25) facing towards the fluid-carrying line (1; 24) has a sealing cone (58) to the sample fluid channel (26). For further improvement of the sealing characteristics and as a possible thermal insulator, it is possible for a sample core gasket seat (60), preferably made of Teflon or a similar material, to be used. The gasket (75) offers a sealing possibility of the stationary attachment unit (52) with respect to the installation site. With the closing screw thread (57), the closing element (53) is opened maximally up to a limit stop (61) or to unscrewing protection (50).

The closing element (53) itself has a metallic sample core (55) that is fully enclosed around the circumference by a handle with insulation (54).

With a rotational movement of the handle (54/15), the sample core (55) moves by means of the closing screw thread (57) and releases the cone gasket (58) so that sample fluid reaches the sample liquid channel (26) via the sample inlet channel (59) which has a T-shaped arrangement.

The connection of the metallic sample core (55) to the insulating handle (54), which is preferably made of plastic, is made in a form-fit manner by means of a receptacle (56), which can be executed as a latching or knurled receptacle.

The signal unit (67) is introduced with a heat-conducting pot (62) in the core (55) in a form-fit manner and, by means of a signal unit latching (65), is inserted into the handle (54) and in this way connected to the closing element (53).

The signal unit (67) is a two-piece connected unit whose lower heat-conducting pot is connected to the signal button sleeve (63) by means of a latching (66). Inserted within the signal unit (67) in the heat-conducting pot (62) is a shape memory spring (68), which, when working, moves a signal button guide (64) in such a manner that the signal button (18) protrudes distinctly beyond the edge of the signal button sleeve (63). In the resting phase, the signal button guide (64) is pressed back by the reset spring (69).

The signal button (18) and the signal button guide (64) have a form-fit connection to each other and can, due to the dimensioning of the limit stop (70) and the depth and color of the collar (76), on the one hand supply an unambiguous working signal and on the other hand be adjusted to different temperatures.

The sample core (55) is heated during the entry of the flame (21) into the sample fluid channel (26) (not shown). The heat transfer likewise increases the temperature of the heat-conducting pot (62) in which the shape memory spring (68) is arranged. As the temperature increases, the shape memory spring (68) presses against the limit stop (70) the signal button guide (64) outwards in such a manner that a clear movement of the signal button (18) to beyond the sleeve (63) occurs.

The signal button guide (64) is preferably depicted in a color other than that of the signal button (18) so that a color change is also discernible after the clear movement beyond the sleeve (63).

During the cooling of the shape memory spring (68), a reset spring (69) presses the signal button against the collar (7) into the resting position.

After the flaming process and registration of the signal button indication, the universal adapter (4) can be stuck onto the receptacle (16) and locked on the groove (17) by means of the locking device (33). For this purpose the locking device (33) is set in the "open" position so that the cylindrical attachment position (46) allows the adapter (4) to be slid on. The position of the locking device is also apparent in the mark on the locking device vanes (48).

Pressing down on the locking device (33) causes lateral guiding and fixation in the groove (17). In the attached state, the line (5) can be connected to the connection (37) and the closing element (53) can be opened in such a way that the sample fluid can be extracted.

LEGEND

| | |
|---|---|
| 1. | Fluid-carrying line |
| 2. | Valve with sample intake |
| 3. | Sampling point valve |
| 4. | Sample adapter |
| 5. | Connection line |
| 6. | Three-way valve |
| 7. | Container connection with hose clip |
| 8. | Sample container |
| 9. | Flushing connection |
| 10. | Connection block with clamp connections |
| 11. | Dead-space-free clamp connections |
| 12. | O-ring holder |
| 13. | Spanner flat |
| 14. | Anti-twisting lock |
| 15. | Twist grip |
| 16. | Retaining sleeve for sample adapter |
| 17. | Locking groove |
| 18. | Signal button |
| 19. | Flaming device |
| 20. | Centering sleeve |
| 21. | Flame |
| 22. | Connection block with hose connections |
| 23. | Hose nozzles |
| 24. | Fluid channel |
| 25. | Front face of sampling point valve |
| 26. | Sample fluid channel |
| 27. | Auxiliary spanner flat |
| 28. | Connection block with weld-on connection pieces |
| 29. | Weld-on connection pieces |
| 30. | Mounting screws for anti-twisting lock |
| 31. | Extraction coupler with closing valve |
| 32. | Screw-in thread |
| 33. | Locking device |
| 34. | Staggered gasket |
| 35. | Opening bolt |
| 36. | Fluid channels |

-continued

| | | |
|---|---|---|
| 37. | Hose connection for sample adapter | |
| 38. | Channel for sample fluid | |
| 39. | Locking groove for extraction coupler | |
| 40. | Star-shaped closing valve | |
| 41. | Gasket for closing valve | |
| 42. | Pressure spring | |
| 43. | Coupler closing piece | |
| 44. | Coupler fitting piece | |
| 45. | Gasket for closing and fitting piece | |
| 46. | Locking device attachment position | |
| 47. | Locking device guide | |
| 48. | Locking device vane | |
| 49. | Adapter sleeve | |
| 50. | Unscrewing protection/limit stop | |
| 51. | Gasket seat | |
| 52. | Stationary attachment unit | |
| 53. | Closing element | |
| 54. | Handle with insulation | |
| 55. | Sample core | |
| 56. | Insulation receptacle | |
| 57. | Closing screw thread | |
| 58. | Sealing cone | |
| 59. | Sample inlet channel | |
| 60. | Sample core gasket seat | |
| 61. | Unscrewing limit stop | |
| 62. | Heat-conducting pot | |
| 63. | Signal button sleeve | |
| 64. | Signal button guide | |
| 65. | Signal unit latching | |
| 66. | Heat-conducting pot latching | |
| 67. | Signal unit | |
| 68. | Shape memory spring | |
| 69. | Reset spring | |
| 70. | Spring stop | |
| 71. | Core gasket | |
| 72. | Screw thread or lock insert | |
| 73. | Clamp | |
| 74. | Fitting front piece | |
| 75. | Gasket seat | |
| 76. | Collar of signal button | |
| 77. | | |

The invention claimed is:

1. A sampling point valve, comprising:
a valve body that can be moved in a valve housing between a closed position and an open position of the sampling point valve,
wherein the valve body has a sample fluid channel,
wherein the valve body is made of a material with a high thermal conductivity coefficient,
wherein a signal unit with an essentially pot-shaped housing part made of a material with a high thermal conductivity coefficient, is in contact with the valve body, and
wherein the signal unit includes a signal button that can be advanced out of a housing by a shape memory spring as it is heated,
wherein arranged in the housing in a manner that allows it to be slid is a guide body, wherein attached on a free end of the guide body is the signal button,
wherein furthermore arranged in the housing is a reset spring that has a smaller spring force than that of the shape memory spring and that preloads the guide body in a retracted starting position.

2. Sampling point valve according to claim 1, wherein sitting on the outside of the valve body is a handle made of a heat-insulating material.

3. Sampling point valve according to claim 2, wherein the housing consists of the pot-shaped housing part and a plastic housing part connected thereto and is set into the handle.

4. Sampling point valve according to claim 1, wherein the guide body is provided with a collar.

5. Sampling point valve according to claim 4, wherein the shape memory spring is supported on a base of the pot-shaped housing part and on the collar.

6. Sampling point valve according to claim 2, wherein a color of the signal button differs from that of the guide body and that with corresponding heating of the valve body the signal button and the free end of the guide body can be advanced beyond the handle.

7. Sampling point valve according to claim 1, wherein the valve body has on a front end a sealing cone with which a sample inlet opening of the valve housing can be tightly closed.

8. Sampling point valve according to claim 1, wherein the valve body is screwed into the valve housing.

9. Sampling point valve according to claim 2, wherein attachable on a free end section of the handle is a sample adapter which has a hose connection.

10. Sampling point valve according to claim 1, wherein the valve body and signal unit housing part are made of metal.

* * * * *